(12) United States Patent
Fujita et al.

(10) Patent No.: US 10,212,776 B2
(45) Date of Patent: Feb. 19, 2019

(54) LIGHT RECEIVING DEVICE AND LIGHT EMITTING AND RECEIVING DEVICE

(71) Applicant: ASAHI KASEI MICRODEVICES CORPORATION, Tokyo (JP)

(72) Inventors: Hiromi Fujita, Tokyo (JP); Yoshiki Sakurai, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 15/850,271

(22) Filed: Dec. 21, 2017

(65) Prior Publication Data

US 2018/0184503 A1 Jun. 28, 2018

(30) Foreign Application Priority Data

Dec. 28, 2016 (JP) .................................. 2016-255817
Dec. 19, 2017 (JP) .................................. 2017-242460
Dec. 19, 2017 (JP) .................................. 2017-242461

(51) Int. Cl.
*G01J 5/00* (2006.01)
*G01N 25/12* (2006.01)
*H05B 33/08* (2006.01)
*H01L 31/0203* (2014.01)
*H01L 31/02* (2006.01)
(Continued)

(52) U.S. Cl.
CPC ......... *H05B 33/0854* (2013.01); *G01N 25/56* (2013.01); *H01L 31/0203* (2013.01); *H01L 31/02019* (2013.01); *H01L 31/02162* (2013.01); *H01L 31/162* (2013.01); *H01L 31/167* (2013.01); *H05B 33/04* (2013.01);
(Continued)

(58) Field of Classification Search
CPC ......... G01J 5/00; G01K 13/00; G01N 27/223; G01N 22/04; G01N 25/12; G01N 27/048; G01M 11/30; G01M 11/31; G02B 6/02204
USPC ........... 374/120, 130, 160, 100, 16, 28, 208; 356/43, 44
See application file for complete search history.

(56) References Cited

U.S. PATENT DOCUMENTS 5,045,683 A 9/1991 Kanda
5,640,234 A * 6/1997 Roth .................. G01N 21/7703
250/227.14
(Continued)

FOREIGN PATENT DOCUMENTS

JP S54-002455 U1 1/1979
JP H02-295542 A 12/1990
(Continued)

*Primary Examiner* — Gail Kaplan Verbitsky
(74) *Attorney, Agent, or Firm* — Morgan, Lewis & Bockius LLP (57) ABSTRACT

A light receiving device including: a light receiving element configured to receive at least a portion of light incident from an outside and output an output signal corresponding to amount of received light; a molded resin portion configured to seal at least a portion of the light receiving element; a temperature information acquiring unit configured to acquire temperature information; a humidity information calculating unit configured to calculate humidity information, based on information relating to at least either electrical characteristics or optical characteristics of the light receiving element and the temperature information; and a compensating unit configured to compensate the output signal, based on the temperature information and the humidity information.

18 Claims, 3 Drawing Sheets

(51) Int. Cl.
  *H01L 31/16* (2006.01)
  *H01L 31/167* (2006.01)
  *G01N 25/56* (2006.01)
  *H01L 31/0216* (2014.01)
  *H05B 33/04* (2006.01)
  *H05B 37/02* (2006.01)
  *G01J 5/10* (2006.01)

(52) U.S. Cl.
  CPC ..... *H05B 33/0842* (2013.01); *H05B 33/0851* (2013.01); *H05B 37/0227* (2013.01); *G01J 5/10* (2013.01)

(56) References Cited

U.S. PATENT DOCUMENTS

| | | | | |
|---|---|---|---|---|
| 6,164,817 | A * | 12/2000 | Trainer | G01N 25/68 374/18 |
| 7,736,051 | B2 * | 6/2010 | Kanai | G01N 25/68 374/121 |
| 8,602,640 | B2 * | 12/2013 | Chiarello | G01N 21/43 356/72 |
| 9,049,998 | B2 * | 6/2015 | Brumback | A61B 5/02433 |
| 9,618,421 | B2 * | 4/2017 | Sanchez | G01M 11/30 |
| 2005/0121614 | A1 * | 6/2005 | Stuttard | G01N 21/3504 250/343 |
| 2011/0061445 | A1 * | 3/2011 | Roehr | B60S 1/0866 73/29.02 |
| 2012/0024042 | A1 * | 2/2012 | Vass | G01N 33/0031 73/23.34 |
| 2012/0035875 | A1 * | 2/2012 | Gordon | G01N 27/223 702/65 |
| 2013/0003070 | A1 * | 1/2013 | Sezaki | G01N 21/554 356/445 |
| 2013/0055697 | A1 * | 3/2013 | Deguchi | G01N 21/65 60/39.24 |
| 2014/0135631 | A1 * | 5/2014 | Brumback | A61B 5/02438 600/479 |
| 2014/0286376 | A1 * | 9/2014 | Ido | G01J 5/0896 374/130 |
| 2014/0369377 | A1 * | 12/2014 | Sakami | G01N 25/64 374/28 |
| 2016/0231244 | A1 | 8/2016 | Camargo et al. | |

FOREIGN PATENT DOCUMENTS

| | | | | |
|---|---|---|---|---|
| JP | H09-033431 | A | | 2/1997 |
| JP | 2004-290412 | A | | 10/2004 |
| JP | 2005-147859 | A | | 6/2005 |
| JP | 2006-038721 | | * | 2/2006 ............. G01N 21/35 |
| JP | 2006-038721 | A | | 2/2006 |
| JP | 2011-058929 | A | | 3/2011 |
| JP | 2011-080772 | A | | 4/2011 |
| JP | 2011-203004 | | * | 10/2011 ............. G01J 1/02 |
| JP | 2012-215432 | A | | 11/2012 |
| JP | 0201497712 | A | * | 10/2014 |
| JP | 2016-143718 | | * | 8/2016 ............. H01L 31/10 |
| JP | 2016-152259 | | * | 8/2016 ............. H01L 31/30 |

* cited by examiner

LIGHT RECEIVING DEVICE AND LIGHT EMITTING AND RECEIVING DEVICE

CROSS REFERENCE TO RELATED APPLICATIONS AND INCORPORATION BY REFERENCE

This application claims benefit of priority under 35 USC 119 based on Japanese Patent Application No. 2016-255817 filed on Dec. 28, 2016, Japanese Patent Application No. 2017-242460 filed on Dec. 19, 2017, and, Japanese Patent Application No. 2017-242461 filed on Dec. 19, 2017, the entire contents of which are incorporated by reference herein.

TECHNICAL FIELD

The present invention relates to a light receiving device and a light emitting and receiving device.

BACKGROUND ART

Conventionally, as applications of optical measurement technology of physical quantities using a light receiving device and a light emitting device, ranging sensors for measuring a distance to a detection target object and gas concentration measuring apparatuses for measuring the concentration of measurement target gas in the atmosphere have been proposed.

In particular, as gas concentration measuring apparatuses, non-dispersive infrared gas concentration measuring apparatuses for, using a feature that an absorption wavelength of a gas differs from gas to gas in a mid-infrared region, measuring gas concentration by detecting the amount of the absorption by a gas have been known. Gas concentration measuring apparatuses using this principle include, for example, an apparatus configured to, by combining a filter (transmission member) through which infrared rays limited to wavelengths at which measurement target gas has absorption characteristics are transmitted and an infrared sensor and measuring the amount of absorption of the infrared rays, measure concentration of the gas (see, for example, JP H09-33431 A).

SUMMARY

According to an aspect of the present invention, there is provided a light receiving device including: a light receiving element configured to receive at least a portion of light incident from an outside and output an output signal corresponding to amount of received light; a molded resin portion configured to seal at least a portion of the light receiving element; a temperature information acquiring unit configured to acquire temperature information; a humidity information calculating unit configured to calculate humidity information, based on information relating to at least either electrical characteristics or optical characteristics of the light receiving element and the temperature information; and a compensating unit configured to compensate the output signal, based on the temperature information and the humidity information.

According to another aspect of the present invention, there is provided a light emitting and receiving device including: a light emitting element; a light receiving element configured to receive at least a portion of light output by the light emitting element and output an output signal corresponding to amount of received light; a molded resin portion configured to seal at least a portion of the light receiving element; a temperature information acquiring unit configured to acquire temperature information; a humidity information calculating unit configured to calculate humidity information, based on information relating to at least either electrical characteristics or optical characteristics of the light receiving element and the temperature information; and a controlling unit configured to control the light emitting element, based on the temperature information and the humidity information.

DETAILED DESCRIPTION

When such an optical measurement apparatus is configured, it is required to eliminate influence of temperature and humidity of an environment as much as possible to maintain required accuracy, and thus package technologies, such as a ceramic package and a can package, have been conventionally used. On the other hand, resin molding technology, which is widely used for integrated circuits and the like, although being an excellent technology that enables production in large quantity and at low cost, is liable to, being influenced by thermal stress caused by a thermal expansion difference between resin material and a light receiving element and light emitting element and swelling stress caused by moisture absorption by resin due to humidity or drying of resin, cause variation in the amount of light emission from the light emitting element and an output signal from the light receiving element. For this reason, conventional molding technologies have a problem in that light sources, sensors, gas sensors, and the like that have high accuracy cannot be achieved.

Embodiments have been made in consideration of the above-described problem, and an object of the embodiments is to provide a light receiving device and a light emitting and receiving device in which influence of temperature and humidity is compensated for and that have high accuracy.

Hereinafter, a mode for embodying the present invention (hereinafter, referred to as the present embodiment) will be described. It should be understood that the following embodiment does not limit the scope of the invention set forth in CLAIMS to the embodiments. In addition, all combinations of features described in the embodiment are not always indispensable for the solution proposed by the invention.

<Light Receiving Device>

A light receiving device according to the present embodiment includes a light receiving element configured to receive at least a portion of light incident from the outside and output an output signal corresponding to the amount of received light, a molded resin portion configured to seal at least a portion of the light receiving element, a temperature information acquiring unit configured to acquire temperature information, a humidity information calculating unit configured to, based on information relating to at least either electrical characteristics or optical characteristics of the light receiving element and the temperature information, calculate humidity information, and a compensating unit configured to compensate the output signal, based on the temperature information and the humidity information.

The light receiving device according to the present embodiment enables influence of variation in the output signal from the light receiving element due to temperature and humidity to be compensated for, which enables optical measurement of a physical quantity to be achieved with higher accuracy than conventional technologies. As an example, since use of the light receiving device according to the present embodiment for a non-dispersive infrared gas concentration measuring apparatus enables the amount of infrared ray absorption by measurement target gas to be measured with high accuracy, it becomes possible to improve measurement accuracy of gas concentration. As used herein, the light incident from the outside means light incident from a light source spatially separated from the light receiving element.

<Light Emitting Device>

A light emitting device according to the present embodiment includes a light emitting element, a molded resin portion configured to seal at least a portion of the light emitting element, a temperature information acquiring unit, a humidity information calculating unit configured to, based on information relating to at least either electrical characteristics or optical characteristics of the light emitting element and the temperature information, calculate humidity information, and a controlling unit configured to control the light emitting element, based on the temperature information and the humidity information.

The light emitting device according to the present embodiment enables influence of variation in the amount of light emission from the light emitting element due to temperature and humidity to be compensated for, which enables optical measurement of a physical quantity to be achieved with higher accuracy than conventional technologies. As an example, since use of the light emitting device according to the present embodiment for a non-dispersive infrared gas concentration measuring apparatus enables infrared rays with a highly accurate amount of light emission to be radiated to measurement target gas, it becomes possible to improve measurement accuracy of gas concentration.

<Light Emitting and Receiving Device>

A light emitting and receiving device according to the present embodiment includes a light emitting element, a light receiving element configured to receive at least a portion of light output by the light emitting element and output an output signal corresponding to the amount of received light, a molded resin portion configured to seal at least a portion of the light emitting element, a temperature information acquiring unit configured to acquire temperature information, a humidity information calculating unit configured to, based on information relating to at least either electrical characteristics or optical characteristics of the light emitting element and the temperature information, calculate humidity information, and a compensating unit configured to compensate the output signal, based on the temperature information and the humidity information.

The light emitting and receiving device according to the present embodiment enables influence of variation in the output signal from the light receiving element and the amount of light emission from the light emitting element due to temperature and humidity to be compensated for, which enables optical measurement of a physical quantity to be achieved with higher accuracy than conventional technologies. As an example, since use of the light emitting and receiving device according to the present embodiment for a non-dispersive infrared gas concentration measuring apparatus enables infrared rays with a highly accurate amount of light emission to be radiated to measurement target gas and the amount of infrared ray absorption by the measurement target gas to be measured with high accuracy, it becomes possible to improve measurement accuracy of gas concentration. By using infrared absorption due to impurities in liquid, it also becomes possible to configure a measurement apparatus that is capable of measuring impurity concentration in the liquid with high accuracy.

Hereinafter, the respective constituent components of the light receiving device, the light emitting device, and the light emitting and receiving device according to the present embodiment will be described taking examples.

<Light Receiving Element>

The light receiving element in the light receiving device and the light emitting and receiving device according to the present embodiment is not limited to a specific one as long as having a sensitivity in a band of light including a wavelength appropriate for a use purpose. In particular, when the light receiving element is used as a gas concentration measuring apparatus, the light receiving element is not limited to a specific one as long as having a sensitivity in a band of light including a wavelength at which the light is absorbed by gas to be detected.

For the light receiving element, a thermal sensor, such as a pyroelectric sensor, a thermopile, and a bolometer, a quantum sensor, such as a photodiode and a phototransistor, and the like are suitable. The light receiving element may further include an optical filter that has desirable optical characteristics suitable for measurement target gas. When the gas to be detected is, for example, carbon dioxide gas, the light receiving element is preferably configured to be mounted with a bandpass filter that is capable of filtering infrared rays in a wavelength range (representatively around 4.3 μm) in which a large amount of infrared ray absorption by the carbon dioxide gas occurs.

The inventors of the present invention have newly found this time that, when at least a portion of the light receiving element is sealed by molded resin, influence of at least either moisture absorption or drying of the molded resin portion causes stress applied to the light receiving element to vary, which causes the output from the light receiving element to vary. Through this finding, the inventors have revealed that measurement of information having a correlation with humidity of the molded resin portion (humidity information) enables influence of variation in the output signal from the light receiving element due to the moisture absorption of the molded resin portion to be compensated for.

As will be described later, the inventors have also newly found that it is possible to calculate information having a correlation with humidity of the molded resin portion (humidity information), based on temperature information and information relating to at least either electrical characteristics or optical characteristics of the light receiving element. Because of this finding, it becomes possible to, by measuring information relating to at least either electrical characteristics or optical characteristics of the light receiving element, acquire information having a correlation with humidity of the molded resin portion (humidity information) and to, using the acquired temperature information and humidity information, compensate the output from the light receiving element.

In the light receiving device and the light emitting and receiving device according to the present embodiment, the light receiving element may have a diode structure that includes indium, includes at least either arsenic or antimony, and has at least a P-type semiconductor layer and an N-type semiconductor layer or may be a resistor. This configuration enables, in a gas concentration measuring apparatus that measures concentration of, in particular, $CO_2$, infrared rays in a wavelength range around 4.3 μm, which is a $CO_2$ absorption wavelength range, to be measured with a high S/N ratio. In addition, in the light receiving device and the light emitting and receiving device according to the present embodiment, the light receiving element may include an auxiliary element, as will be described later.

<Light Emitting Element>

The light emitting element in the light emitting device and the light emitting and receiving device according to the present embodiment is not limited to a specific one as long as outputting light including a wavelength appropriate for a use purpose. In particular, when being used as a gas concentration measuring apparatus, the light emitting element is not limited to a specific one as long as outputting light including a wavelength at which the light is absorbed by gas to be detected. Specific examples of the light emitting element include a micro electro mechanical systems (MEMS) heater and a light emitting diode (LED). Such a light emitting element may, from a standpoint of reducing noise due to light absorption by components other than the gas to be detected, output only light having a wavelength range in which a large amount of light is absorbed by the gas to be detected.

From a standpoint that a light emitting wavelength range can be controlled by the band gap of a light emitting layer, the light emitting element preferably has an LED structure. When a light source with the LED structure is used, adjustment of the band gap of a material used for the light emitting layer to the absorption wavelength of the gas to be detected enables a specific gas to be detected without using an optical filter (for example, a bandpass filter), which enables a gas sensor without optical filter to be achieved. The achievement of a gas sensor without optical filter enables the structure of the gas concentration measuring apparatus to be simplified.

The inventors of the present invention have newly found this time that, when at least a portion of the light emitting element is sealed by molded resin, influence of at least either moisture absorption or drying of the molded resin portion causes stress applied to the light emitting element to vary, which causes the amount of light emission from the light emitting element to vary. Therefore, measurement of information having a correlation with humidity of the molded resin portion (humidity information) enables influence of variation in the amount of light emission from the light emitting element due to the moisture absorption of the molded resin portion to be compensated for.

As will be described later, the inventors have also newly found that it is possible to calculate information having a correlation with humidity of the molded resin portion (humidity information), based on temperature information and information relating to at least either electrical characteristics or optical characteristics of the light emitting element. Because of this finding, it becomes possible to, by measuring information relating to at least either electrical characteristics or optical characteristics of the light emitting element, acquire information having correlation with humidity of the molded resin portion (humidity information) and to, using the acquired temperature information and humidity information, control the output from the light emitting element.

In the light emitting device and the light emitting and receiving device according to the present embodiment, the light emitting element may have a diode structure that includes indium, includes at least either arsenic or antimony, and has at least a P-type semiconductor layer and an N-type semiconductor layer. This configuration enables, in a gas concentration measuring apparatus that measures concentration of, in particular, $CO_2$, the amount of infrared emission in a wavelength range around 4.3 μm, which is a $CO_2$ absorption wavelength range, to be increased.

In addition, in the light emitting device and the light emitting and receiving device according to the present embodiment, the light emitting element may include an auxiliary element, as will be described later.

<Temperature Information Acquiring Unit>

The temperature information acquiring unit in the light receiving device according to the present embodiment acquires temperature information of the light receiving device. In this case, the temperature information may include information relating to temperature of the light receiving element or temperature of the molded resin portion. In this case, the temperature information may also include information relating to at least either electrical characteristics or optical characteristics of the light receiving element.

The temperature information acquiring unit in the light emitting device according to the present embodiment acquires temperature information of the light emitting device. In this case, the temperature information may include information relating to temperature of the light emitting element or temperature of the molded resin portion. In this case, the temperature information may also include information relating to at least either electrical characteristics or optical characteristics of the light emitting element.

The temperature information acquiring unit in the light emitting and receiving device according to the present embodiment acquires temperature information of the light emitting and receiving device. In this case, the temperature information may include information relating to at least one of temperature of the light receiving element, temperature of the light emitting element, and temperature of the molded resin portion. In this case, the temperature information may also include information relating to at least either electrical characteristics or optical characteristics of at least either the light receiving element or the light emitting element.

When the light receiving device, the light emitting device, or the light emitting and receiving device according to the present embodiment further includes an auxiliary element, which will be described later, at least a portion of which is sealed by a molded resin portion, the temperature information may include information relating to at least either electrical characteristics or optical characteristics of the auxiliary element.

When, in particular, variation in temperature of a measurement environment is fast or an equilibrium state between the light receiving element and/or light emitting element and the measurement environment is not maintained, information relating to the temperature of the light receiving element and/or light emitting element may be used as the temperature information.

When, on the contrary, variation in the temperature of the measurement environment is slow or an equilibrium state between the light receiving element and/or light emitting element and the measurement environment is maintained, the temperature of the environment may be measured by using a temperature sensor, separately disposed on, for example, a substrate on which the light receiving element or the light emitting element is fabricated, and the like, and the measured temperature may be used as the temperature information.

As a means for acquiring the temperature information in this case, temperature sensors, specifically, a thermistor, a platinum (Pt) resistance temperature detector, and a diode, may be used.

In addition, the temperature information that the temperature information acquiring unit acquires is not limited to temperature itself and may be calculated based on electrical characteristics and optical characteristics of the light receiving element and/or the light emitting element that are physical quantities influenced by temperature. As used herein, the electrical characteristics means physical quantities that characterize characteristics of the light emitting element and the light receiving element, such as current-voltage characteristics, output resistance (internal resistance) around zero bias, which is acquired from the current-voltage characteristics, and forward voltage drop. In addition, the optical characteristics means physical quantities that characterize characteristics of the light emitting element and the light receiving element, such as the amount of light emission from the light emitting element and photocurrent (output signal) in the light receiving element. Although the physical quantities are influenced by factors other than temperature, required information (humidity information) can be extracted from the physical quantities by the humidity information calculating unit, the compensating unit, and the controlling unit, which will be described later. For this reason, use of the physical quantities enables compensation of the output signal and control of the light emitting element to be performed.

Hereinafter, each of the electrical characteristics and the optical characteristics of the light receiving element and the light emitting element mean the above-described physical quantities.

The temperature information acquiring unit in the light emitting and receiving device according to the present embodiment outputs the acquired the temperature information to the compensating unit and the humidity information calculating unit, which will be described later. As used herein, the "temperature information" that is output to the compensating unit and the "temperature information" that is output to the humidity information calculating unit are not limited to information having the same format as long as being information (data) related to the temperature. It goes without saying that the scope of the present invention includes an embodiment in which first temperature information and second temperature information different from the first temperature information are obtained from identical temperature information by correcting it by using different correction formulae, and output to the compensating unit and the humidity information calculating unit, respectively. In addition, the forward voltage drop of the light emitting element may be output to the humidity information calculating unit as the temperature information, and an output of an outside temperature sensor or a temperature sensor on the same mount substrate may be acquired by the temperature information acquiring unit and output to the compensating unit as the temperature information. It is certain that an output of a temperature sensor disposed outside the light emitting and receiving device or on the same mount substrate may be acquired by the temperature information acquiring unit and output to the compensating unit the humidity information calculating unit as "common" temperature information.

The same applies to the cases of the temperature information acquiring unit in the light emitting device according to the present embodiment, and the temperature information acquiring unit in the light receiving device according to the present embodiment. In addition, the same applies to the temperature information output from the temperature information acquiring unit to the controlling units in the light emitting device and the light emitting and receiving device.

<Humidity Information Calculating Unit>

The humidity information calculating unit in the light receiving device according to the present embodiment calculates humidity information, based on temperature information and information relating to at least either electrical characteristics or optical characteristics of the light receiving element. The calculation enables the light receiving device to obtain humidity information for compensating for variation in the characteristics of the light receiving element caused by moisture absorption and drying of molded resin. In this case, the humidity information may also include information relating to at least either electrical characteristics or optical characteristics of the light receiving element.

The humidity information calculating unit in the light emitting device according to the present embodiment calculates humidity information, based on temperature information and information relating to at least either electrical characteristics or optical characteristics of the light emitting element. The calculation enables the light emitting device to obtain humidity information for compensating for variation in the characteristics of the light emitting element caused by moisture absorption and drying of molded resin. In this case, the humidity information may also include information relating to at least either electrical characteristics or optical characteristics of the light emitting element.

The humidity information calculating unit in the light emitting and receiving device according to the present embodiment calculates humidity information, based on temperature information and information relating to at least either electrical characteristics or optical characteristics of each of the light emitting element and the light receiving element. The calculation enables the light emitting and receiving device to obtain humidity information for compensating for variation in the characteristics of the light receiving element and the light emitting element caused by moisture absorption and drying of molded resin. In this case, the humidity information may also include information relating to at least either electrical characteristics or optical characteristics of at least either the light receiving element or the light emitting element.

When the light receiving device, the light emitting device, or the light emitting and receiving device according to the present embodiment further includes an auxiliary element (details thereof will be described later) at least a portion of which is sealed by a molded resin portion, the humidity information may be calculated based on temperature information and information relating to at least either electrical characteristics or optical characteristics of the auxiliary element. In this case, the humidity information may include information relating to at least either electrical characteristics or optical characteristics of the auxiliary element.

As the auxiliary element, for example, a diode or a resistor disposed in the molded resin portion or at least either a diode or a resistor formed of the same material as the light receiving element and the light emitting element may be used.

The electrical characteristics and the optical characteristics of the light receiving element, the light emitting element, or the auxiliary element, used for calculating the humidity information, are influenced by not only humidity but also temperature. Therefore, elimination of such temperature dependency based on the temperature information enables the humidity information to be calculated.

As described afore, the humidity information that the humidity information calculating unit calculates is not limited to humidity itself and may be information relating to electrical characteristics or optical characteristics, both of which are physical quantities that are influenced by swelling stress caused by moisture absorption of the molded resin portion due to humidity, or a combination thereof.

Although the physical quantities are influenced by temperature, the compensating unit and the controlling unit, which will be described later, are capable of reducing influence of temperature from the physical quantities and extracting information (humidity information) on which humidity has a high degree of influence. For example, correction of internal resistance of the light emitting element by use of temperature information enables information that has no temperature dependency and represents the amount of variation in the internal resistance according to states of moisture absorption of molded resin, that is, humidity information, to be obtained. Compensation of the output signal from the light receiving element and control of the light emitting element based on the humidity information enable configuration of a light receiving device, a light emitting device, and a light emitting and receiving device that are compensated for influence of temperature and humidity.

Note that, when electrical characteristics and optical characteristics of the light receiving element and the light emitting element are used as temperature information, it is required to use electrical characteristics and optical characteristics different from the electrical characteristics and optical characteristics that are used for the calculation of humidity information. In the case of, for example, the light emitting device, when the forward voltage drop of the light emitting element is used as temperature information, it is required to use a physical quantity other than the forward voltage drop of the light emitting element (as an example, the internal resistance of the light emitting element, photocurrent of a photodiode provided as of the auxiliary element for the light emitting element, or the line) for the calculation of humidity information. The same applies to the cases of the light emitting device and the light emitting and receiving device.

<Molded Resin Portion>

In the light receiving device, the light emitting device, and the light emitting and receiving device according to the present embodiment, the molded resin portion may seal at least a portion of the light receiving element and at least a portion of the light emitting element. Alternatively, the molded resin portion may seal either at least a portion of the light receiving element or at least a portion of the light emitting element. As a molding material of the molded resin portion, resin molding material, such as epoxy resin and phenol resin, may be used. On this occasion, the resin molding material may include filler materials, such as $SiO_2$ and $Al_2O_3$. In addition, a stress relaxation layer (buffer layer) made of polyimide, polyamide, silicone resin, and the like may be interposed between at least either the light receiving element or the light emitting element and the molded resin portion.

In the light emitting and receiving device of the present embodiment, the molded resin portion may include a light receiving side sealing region sealing at least a portion of the light receiving element and a light emitting side sealing region sealing at least a portion of the light emitting element. In this case, the light receiving side sealing region and the light emitting side sealing region may be spatially in contact with each other.

<Compensating Unit>

In the light receiving device and the light emitting and receiving device according to the present embodiment, the compensating unit is not limited to a specific one as long as being capable of compensating the output signal from the light receiving element, based on temperature information and humidity information. For the compensating unit, for example, an analog IC, a digital IC, a central processing unit (CPU), and the like are suitable.

The temperature information and the humidity information acquired from the temperature information acquiring unit and the humidity information calculating unit are not limited to a temperature value and a humidity value themselves and include information calculated from physical quantities, such as an electrical resistance value and a photocurrent value, the characteristics of which vary influenced by temperature and humidity. In addition, the compensating unit may include a storage area in which data that are calibrated to eliminate influence of temperature and influence of humidity in advance are stored or may fulfill a function for controlling the light emitting element.

<Controlling Unit>

In the light emitting device and the light emitting and receiving device according to the present embodiment, the controlling unit is not limited to a specific one as long as being capable of controlling the light emitting element based on temperature information and humidity information, and a drive circuit that includes, for example, an analog IC, a digital IC, a CPU, and the like is suitable for the controlling unit.

When the light emitting element is an LED, the controlling unit may control, for example, at least one of an input current value, energizing time, and non-energizing time of the light emitting element.

The temperature information and the humidity information acquired from the temperature information acquiring unit and the humidity information calculating unit are not limited to a temperature value and a humidity value themselves and include information calculated from physical quantities, such as an electrical resistance value and a photocurrent value, the characteristics of which vary influenced by temperature and humidity. The controlling unit of the light emitting device may include a storage area in which data that are calibrated to eliminate influence of temperature and influence of humidity in advance are stored or may fulfill a function for compensating the output signal from the light receiving element.

<Auxiliary Element>

The light receiving device, the light emitting device, and the light emitting and receiving device according to the present embodiment may further include an auxiliary element at least a portion of which is sealed by the molded resin portion, and at least either temperature information or humidity information may include information relating to at least either electrical characteristics or optical characteristics of the auxiliary element. As the auxiliary element, for example, a diode or a resistor disposed in the molded resin portion or a diode or a resistor made of the same material as the light receiving element and the light emitting element may be used. In this case, the auxiliary element may be formed on the same substrate as the light receiving element. In this case, a plurality of auxiliary elements may also be arranged on the substrate. The plurality of auxiliary elements may be connected to one another in parallel, in series, or in series-parallel or may form a Wheatstone bridge.

In particular, disposition of the auxiliary element and the light receiving element or the light emitting element on the same substrate enables the temperature of the light receiving element or the light emitting element and temperature of the auxiliary element to be brought close to thermal equilibrium by means of heat conduction via the substrate.

In the light receiving device, the light emitting device, and the light emitting and receiving device according to the present embodiment, since it is generally difficult to avoid different materials being arranged close to each other, influence of thermal stress due to a difference in coefficients of thermal expansion and swelling stress caused by moisture absorption of a sealing portion due to humidity differs depending on positions on the substrate (regions of the substrate) on which the light receiving element or the light emitting element is disposed. In this case, further disposition of a plurality of auxiliary elements at a plurality of positions on the same substrate, measurement of at least either electrical characteristics or optical characteristics of each of the plurality of auxiliary elements, and comparison in and evaluation of variation in the characteristics due to temperature and at least either thermal stress or swelling stress among the plurality of auxiliary elements enable at least either temperature information or humidity information to be acquired. Specifically, acquisition of temperature dependency of at least either electrical characteristics or optical characteristics of the auxiliary elements in a dry state and subsequent acquisition of the same characteristics under a humid environment enable correction parameters for extracting the temperature information and the humidity information to be extracted.

In the above, "on the same substrate" means, when the light receiving element, the light emitting element, or the auxiliary element is mounted on a printed wiring board (mounting board) and are sealed, being mounted on a portion of the printed wiring board that is sealed in a similar manner. Alternatively, when the light receiving element, the light emitting element, or the auxiliary element is formed on a substrate, such as a silicon (Si) substrate, a gallium arsenide (GaAs) substrate, and a glass substrate, "on the same substrate" means being formed on a portion of the substrate that is sealed in a similar manner. When the light receiving element and/or the light emitting element have/has a diode structure including a P-type semiconductor layer and an N-type semiconductor layer, the auxiliary element may have the same diode structure or may be a resistor including a P-type semiconductor layer and an N-type semiconductor layer.

In the light receiving device and the light emitting and receiving device of the present embodiment, the auxiliary element may have a diode structure that includes indium, includes at least either arsenic or antimony, and has at least a P-type semiconductor layer and an N-type semiconductor layer or may be a resistor.

Next, respective embodiments of the present invention will be described with reference to the drawings.

[First Embodiment]

Figure 1:
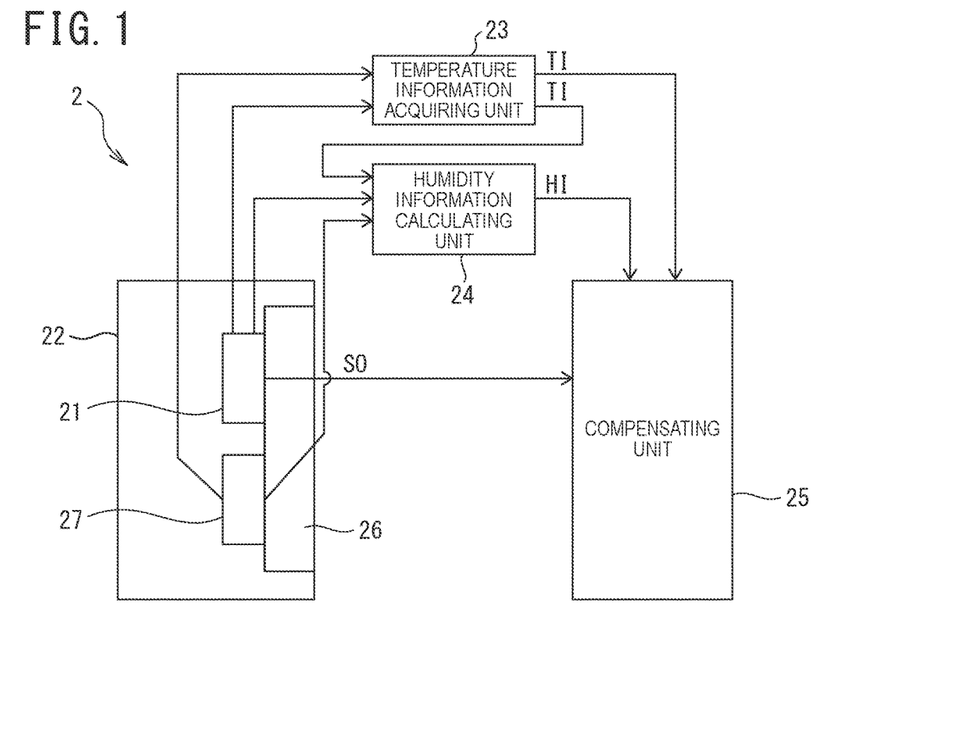
FIG. 1 is a configuration diagram for a description of a light receiving device according to a first embodiment of the present invention.

FIG. 1 is a configuration diagram for a description of a light receiving device according to a first embodiment of the present invention. As illustrated in FIG. 1, a light receiving device 2 of the first embodiment includes a substrate 26, a light receiving element 21 and an auxiliary element 27 formed on the substrate 26, a molded resin portion 22 configured to seal at least a portion of the light receiving element 21, the auxiliary element 27, and the substrate 26, a temperature information acquiring unit 23, a humidity information calculating unit 24, and a compensating unit 25 configured to compensate an output signal SO from the light receiving element 21, based on temperature information TI acquired from the temperature information acquiring unit 23 and humidity information HI acquired from the humidity information calculating unit 24.

[Second Embodiment]

Figure 2:
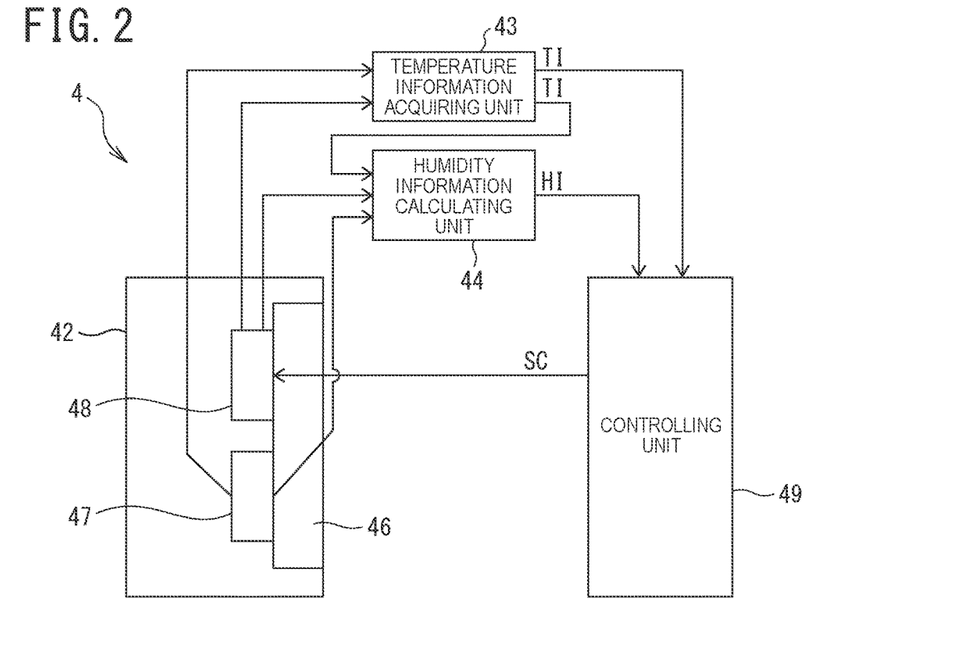
FIG. 2 is a configuration diagram for a description of a light emitting device according to a second embodiment of the present invention.

FIG. 2 is a configuration diagram for a description of a light emitting device according to a second embodiment of the present invention. As illustrated in FIG. 2, a light emitting device 4 of the second embodiment includes a substrate 46, a light emitting element 48 and an auxiliary element 47 formed on the substrate 46, a molded resin portion 42 configured to seal at least a portion of the light emitting element 48, the auxiliary element 47, and the substrate 46, a temperature information acquiring unit 43, a humidity information calculating unit 44, and a controlling unit 49 configured to output a control signal SC for controlling the light emitting element 48, based on temperature information TI acquired from the temperature information acquiring unit 43 and humidity information HI acquired from the humidity information calculating unit 44.

[Third Embodiment]

Figure 3:
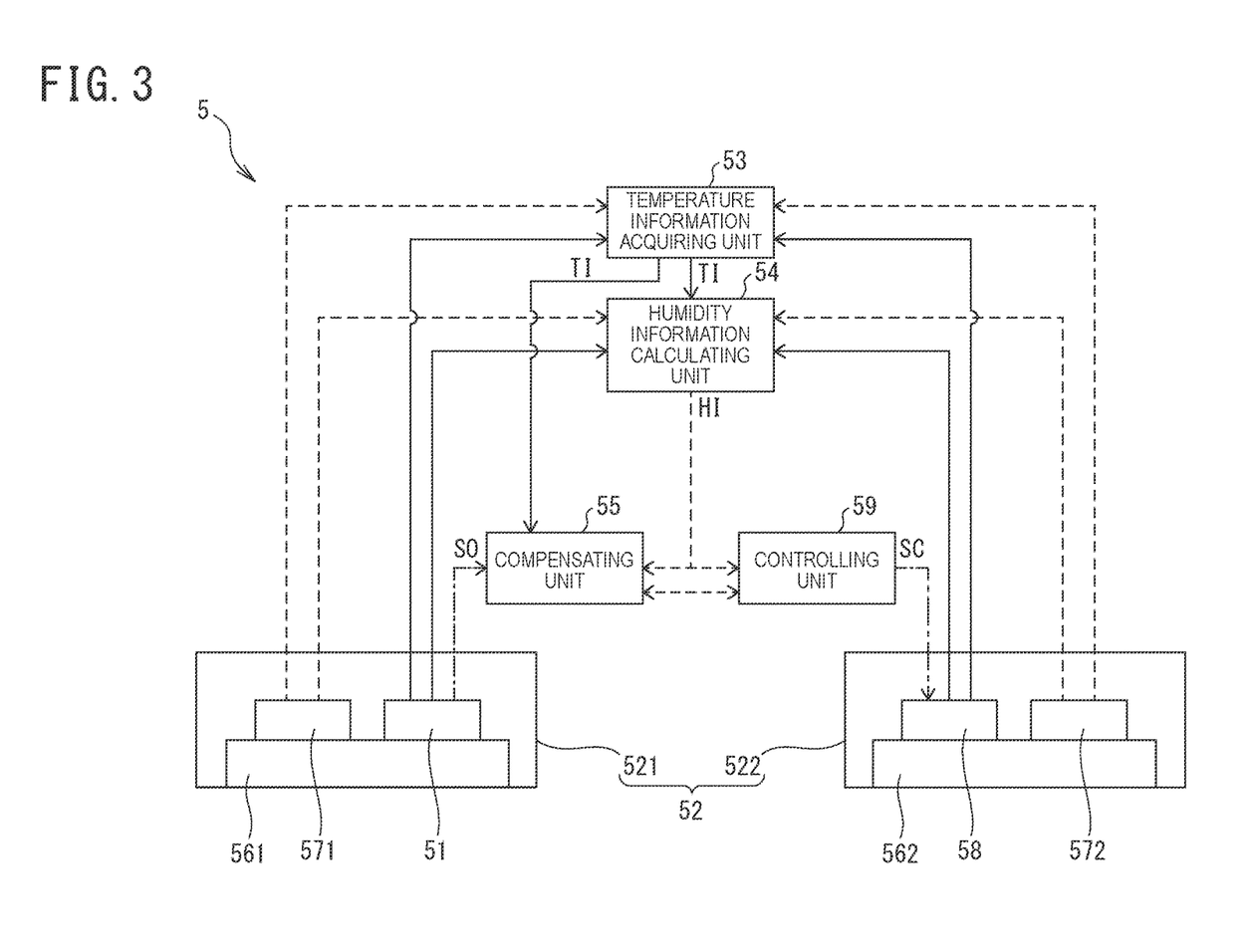
FIG. 3 is a configuration diagram for a description of a light emitting and receiving device according to a third embodiment of the present invention.

FIG. 3 is a configuration diagram for a description of a light emitting and receiving device according to a third embodiment of the present invention. As illustrated in FIG. 3, a light emitting and receiving device 5 according to the third embodiment includes a light receiving side substrate 561, a light receiving element 51 and a light receiving side auxiliary element 571 formed on the light receiving side substrate 561, a light receiving side sealing region 521 configured to seal at least a portion of the light receiving element 51, the light receiving side auxiliary element 571, and the light receiving side substrate 561, a light emitting side substrate 562, a light emitting element 58 and a light emitting side auxiliary element 572 formed on the light emitting side substrate 562, a light emitting side sealing region 522 configured to seal at least a portion of the light emitting element 58, the light emitting side auxiliary element 572, and the light emitting side substrate 562, a temperature information acquiring unit 53, a humidity information calculating unit 54, a compensating unit 55 configured to compensate an output signal SO from the light receiving element 51, based on temperature information TI acquired from the temperature information acquiring unit 53 and humidity information HI acquired from the humidity information calculating unit 54, and a controlling unit 59 configured to output a control signal SC for controlling the light emitting element 58, based on the temperature information TI and the humidity information HI. The light emitting and receiving device 5 includes a molded resin portion 52 made up of the light receiving side sealing region 521 and the light emitting side sealing region 522. The light receiving side sealing region 521 and the light emitting side sealing region 522 are formed spatially separated from each other.

An example of a method for compensating for influence of temperature and humidity in the present invention will now be described using an example in which the light emitting and receiving device 5 according to the third embodiment is applied to a gas concentration measuring apparatus. Specifically, a form in which the light emitting and receiving device 5 according to the third embodiment is installed in a gas cell is assumed. In the above, the gas cell is a structure into which gas to be detected is able to flow due to diffusion with the external environment and that includes an optical path that guides light emitted from a light emitting element to a light receiving element by reflecting or condensing the light using interior mirror planes and the like. The light propagating inside the gas cell is absorbed by the gas according to propagation distance and gas concentration, which attenuates the amount of light reaching the light receiving element. Thus, measurement and evaluation of the amount of variation in the amount of light propagating inside the gas cell enable measurement of gas concentration. A gas concentration measuring apparatus having a configuration of the light emitting and receiving device 5 according to the third embodiment is capable of obtaining a gas concentration calculation formula by means of, as an example, an operation described below.

For temperature information T acquired from the temperature information acquiring unit, for example, temperature acquired from a temperature sensor annexed to the light emitting and receiving device is used. Measurement of temperature dependency of the output from the light receiving element in a condition where, for example, there is no gas to be detected and the atmosphere is in a dry state at a humidity of 0%, based on the temperature information T enables a correction formula for calculating the amount h(T) of correction in correcting the temperature dependency of the output to be obtained. The correction formula can be expressed as the formula (1).

[Formula 1]

$$h(T) = A_1 \times T^2 + B_1 \times T + C_1 \qquad (1)$$

Subsequently, measurement of temperature dependency of internal resistance r(H, T) of the light emitting element in a condition where, for example, there is no gas to be detected and the atmosphere is in a dry state at a humidity of 0%, based on the temperature information T and the internal resistance r(H, T) enables a correction formula for calculating the amount f(H) of correction in correcting the temperature dependency of the internal resistance to be obtained. The correction formula can be expressed as the formula (2).

[Formula 2]

$$f(H) = \frac{r(H, T)}{D_1 \times T^2 + E_1 \times T + F_1} \qquad (2)$$

The amount f(H) of correction is an amount obtainable by eliminating the temperature dependency from the internal resistance of the light emitting element, which varies according to temperature and humidity, and is used as humidity information that varies according to humidity (hereinafter, "f(H)"is also assigned as a reference sign of the humidity information). Alternatively, a polynomial may be constructed based on the humidity information f(H) expressed by the formula (2) and may be used anew as humidity information $f_2(H)$, as expressed by the formula (3). The temperature information TI acquired from the temperature information acquiring unit corresponds to the temperature information TI illustrated in FIG. 3, and the humidity information f(H) and the humidity information $f_2(H)$ correspond to the humidity information HI illustrated in FIG. 3.

[Formula 3]

$$f_2(H) = D_2 \times f(H)^2 + E_2 \times f(H) + F_2 \qquad (3)$$

Subsequently, correction of an output signal $I_{out}$ from the light receiving element based on the amount h(T) of correction acquired from the temperature information TI, which is acquired from the temperature information acquiring unit, and the humidity information f(H) acquired from the humidity information calculating unit, as described below enables an output signal in which influence of temperature and humidity is corrected, that is, gas concentration c, to be calculated.

[Formula 4]

$$c = J \times \left\{ \frac{I_{out}}{f(H) \times h(T)} \right\}^2 + K \times \left\{ \frac{I_{out}}{f(H) \times h(T)} \right\} + L \qquad (4)$$

Constants $A_1$, $B_1$, and $C_1$ in the formula (1), constants $D_1$, $E_1$, and $F_1$ in the formula (2), constants $D_2$, $E_2$, and $F_2$ in the formula (3), and constants J, K, and L in the formula (4) are correction coefficients that are acquired by fitting in advance to eliminate the temperature dependency and the humidity dependency. As to, in particular, the constants J, K, and L, by measuring output signals varying gas concentration of the measurement target gas, coefficients that minimize error are derived. Use of these constants and correction formulae enables the gas concentration c the temperature dependency and humidity dependency of which are corrected to be calculated, based on output signals $I_{out}$ from the light receiving element and internal resistances r of the light emitting element at respective temperature states and respective humidity states.

Correction of the output signal from the light receiving element based on the temperature information and the humidity information in accordance with the above-described process enables a gas concentration measuring apparatus having higher accuracy than conventional gas concentration measuring apparatuses to be achieved.

Although, in the third embodiment, the correction of the output signal from the light receiving element based on output from the temperature information acquiring unit is performed using a quadratic expression, the compensation of calculating humidity information based on the temperature information and the internal resistance of the light emitting element is performed using a quadratic expression, and the compensation of the output signal from the light receiving element 51 for calculating a final gas concentration is performed using a quadratic expression, the configuration is only an example, and the technical scope of the present invention is not limited to the above-described configuration.

As another method, increasing the degree of polynomial for compensation, such as using a quadratic expression in place of a linear expression and a cubic expression in place of a quadratic expression, enables the measurement accuracy of gas concentration to be improved. In addition, the reciprocal of a polynomial, an exponent function, or a logarithm function may be used. On the other hand, since, when the degree of polynomial for compensation is increased or the function for compensation is complicated, the number of measurement points (with respect to temperature, humidity, and gas concentration) required for obtaining a calibration curve increases, the degree of polynomial for compensation or the function for compensation may be determined appropriately in consideration of balance between required accuracy and manufacturing cost. In addition, even if the temperature information includes the humidity information, it is possible to correct an influence of the temperature and the humidity in the signal, by using electrical characteristics and optical characteristics different from those of the humidity information calculating unit and by constructing a correction formula in the compensating unit so as to eliminate the humidity dependency.

[Fourth Embodiment]

A light emitting and receiving device according to a fourth embodiment of the present invention is a light emitting and receiving device in which the light emitting element 58 described in the above-described third embodiment is a mid-infrared LED.

[Fifth Embodiment]

A light emitting and receiving device according to a fifth embodiment of the present invention is a light emitting and receiving device in which the light receiving element 51 and the light receiving side auxiliary element 571 in the above-described third embodiment or fourth embodiment have the same thin film structure. As used herein, the thin film structure is a PIN diode structure in which a P-type semiconductor layer, an I-type semiconductor layer (undoped layer), and an N-type semiconductor layer are stacked. The light receiving element 51 and the light receiving side auxiliary element 571 having the same thin film structure provides advantages in that compensation for variation in characteristics caused by temperature variation is facilitated and a manufacturing process is shortened.

[Sixth Embodiment]

A light emitting and receiving device according to a sixth embodiment of the present invention has a feature such that, in the above-described fourth or fifth embodiment, the light receiving side sealing region 521 configured to seal the light receiving element 51 and the light emitting side sealing region 522 configured to seal the light emitting element 58 are spatially in contact with each other (the light receiving side sealing region 521 and the light emitting side sealing region 522 are formed of a single sealing material). In other words, the light emitting and receiving device according to the sixth embodiment is characterized in including a molded resin portion 52 made up of the light receiving side sealing region 521 and the light emitting side sealing region 522, which are spatially in contact with each other. The light emitting and receiving device according to the sixth embodiment has an advantage in enabling the light receiving element 51 and the light emitting element 58 to be sealed in the same processing step and the manufacturing process to be shortened.

[Seventh Embodiment]

A light receiving device, a light emitting device, and a light emitting and receiving device according to a seventh embodiment of the present invention are characterized in that, in the above-described first to sixth embodiments, a light receiving element, a light emitting element, and an auxiliary element are configured to have a PIN diode structure that includes an active layer (I-layer) formed of an AlInSb layer formed on a GaAs substrate. In the above configuration, a composition ratio of aluminum (Al) in the active layer is in a range from 0 to 20%, and barrier layers for blocking carriers (electrons and holes) may be formed below and above the active layer. Further, below and above the active layer, a P-layer and an N-layer for supplying carriers are formed. Since, when the Al composition ratio is set at a value in a range from 2 to 5%, the above material is capable of absorbing or discharging light corresponding to an infrared absorption wavelength of 4.3 µm of carbon dioxide gas, the material is suitable for a light receiving element and a light emitting element. Alternatively, since, when the Al composition ratio is set at a value in a range from 8 to 10%, the material is capable of absorbing or discharging light corresponding to an infrared absorption wavelength of 3.3 µm of hydrocarbon gas, including methane, the material is suitable for a light receiving element and a light emitting element.

[Eighth Embodiment]

A light receiving device, a light emitting device, and a light emitting and receiving device according to an eighth embodiment of the present invention are characterized in that, in the above-described first to sixth embodiments, a light receiving element, a light emitting element, and an auxiliary element are configured to have a PIN diode structure that includes an active layer (I-layer) formed of an AlInAsSb layer formed on a GaAs substrate. In the above configuration, setting an Al composition ratio and an Sb composition ratio in the active layer at a value in a range from 0 to 5% and at a value in a range from 0 to 5%, respectively, makes the material suitable for detecting water (2.7 µm) or methane (3.3 µm), and increasing the Sb composition ratio to 10 to 13% makes the material suitable for detecting carbon dioxide gas (4.3 µm).

EXAMPLE 1

Next, a light receiving device, a light emitting device, and a light emitting and receiving device according to an example of the present embodiment will be described. The following example is an example in which a light emitting and receiving device of the present embodiment is applied to a carbon dioxide gas concentration measuring apparatus.

A light emitting element (mid-infrared LED light source) sealed in a sealing portion, a quantum-type infrared sensor that has the same thin film structure as the light emitting element, is formed on the same substrate as the light emitting element, and serves as an auxiliary element used for temperature measurement, and a quantum-type infrared sensor serving as a light receiving element were arranged in a dome-shaped gas cell having, on the inside thereof, a spherical surface with a high reflection ratio. The quantum-type infrared sensor serving as a light receiving element has the same thin film structure as the light emitting element.

A temperature information acquiring unit was configured such that an auxiliary element for the light emitting element was connected thereto and a photocurrent output from the auxiliary element was used as temperature information. A humidity information calculating unit was configured such that the light emitting element was connected thereto and internal resistance of the light emitting element was used as humidity information. In the above configuration, the light emitting element and the auxiliary element are sealed in the same molded resin portion, and the configuration of the humidity information calculating unit may thus be altered to a configuration in which, in place of the internal resistance of the light emitting element, values of internal resistance of the auxiliary element are provided to the humidity information calculating unit.

Next, carbon dioxide gases having gas concentrations of 400 ppm, 1000 ppm, and 2000 ppm as a first carbon dioxide gas concentration, a second carbon dioxide gas concentration, and a third carbon dioxide gas concentration, respectively, were selected, a low temperature, a medium temperature, and a high temperature described in the respective embodiments were assumed to be 10° C., 25° C., and 40° C., respectively, and a gas concentration calculation formula was derived based on the respective embodiments, and, using the derived formula, gas concentration calculation at temperatures of 10° C., 25° C., and 40° C. in a dry environment (corresponding to a moisture absorption rate of 0% of the sealing portion) and gas concentration calculation at a temperature of 25° C. in a high humidity environment (corresponding to a moisture absorption rate of 100% of the sealing portion) were performed at carbon dioxide gas concentrations of 400 ppm, 1000 ppm, and 2000 ppm.

Figure 4:
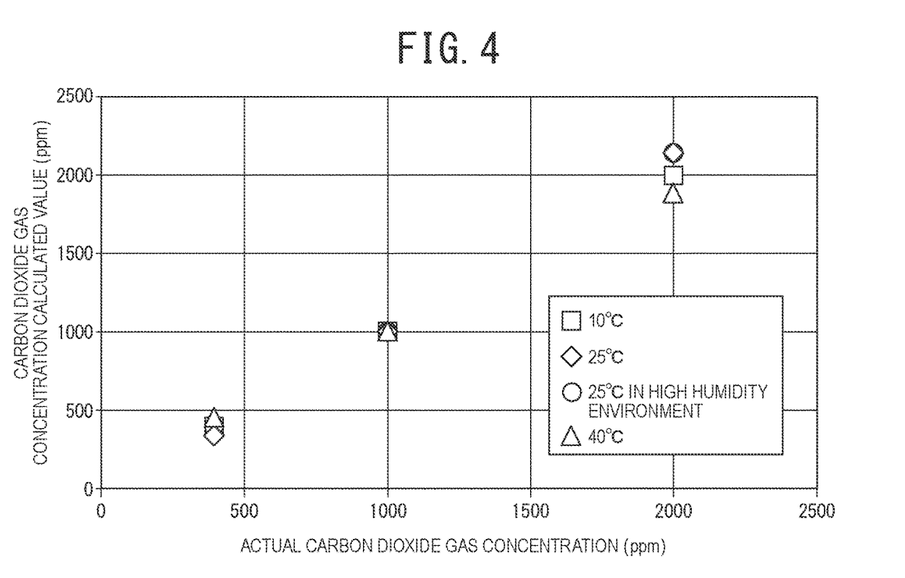
FIG. 4 is a diagram descriptive of a light emitting and receiving device according to an example of embodiments of the present invention and is a diagram illustrative of a relationship between actual concentration of carbon dioxide gas and calculated values of carbon dioxide gas concentration when the light emitting and receiving device is applied to a carbon dioxide gas concentration measuring apparatus.

FIG. 4 is a diagram illustrative of a relationship between actual concentration of carbon dioxide gas and calculated values of carbon dioxide gas concentration in the example. In FIG. 4, the abscissa and the ordinate represent the actual concentration of carbon dioxide gas and the calculated values of carbon dioxide gas concentration, respectively. Square marks, rhombus marks, circle marks, and triangle marks illustrated in FIG. 4 indicate characteristics at 10° C. in the dry environment, characteristics at 25° C. in the dry environment, characteristics at 25° C. in the high humidity environment, and characteristics at 40° C. in the dry environment, respectively.

COMPARATIVE EXAMPLE

A carbon dioxide gas concentration measuring apparatus in a comparative example arranged a light emitting element (mid-infrared LED light source) sealed in a molded resin portion and a quantum-type infrared sensor having the same thin film structure as the light emitting element and serving as a light receiving element in a dome-shaped gas cell having, on the inside thereof, a spherical surface with a high reflection ratio difference from the carbon dioxide gas concentration measuring apparatus according to the example is that the carbon dioxide gas concentration measuring apparatus in the comparative example does not include a humidity information calculating unit.

Next, using Lambert-Beer's formula (5) below, which is a conventional, general gas concentration calculation formula, constants A2 and B2 in the formula were calculated by fitting relationship data between output from the light receiving element at a temperature of 25° C., in a dry environment, and at carbon dioxide gas concentrations of 400 ppm and 2000 ppm and the carbon dioxide gas concentrations to the Lambert-Beer's formula (5) below.

[Formula 5]

$$c = A2 \times \log\left(B2 \frac{I_{ref}}{I_{out}}\right) \quad (5)$$

In the formula (5), "c", "$I_{ref}$", and "$I_{out}$" indicate carbon dioxide gas concentration, output from the temperature information acquiring unit, and output from the light receiving element, respectively. In addition, "A2" and "B2" indicate constants that are calculated from relationships among the output from light receiving element, the output from the temperature information acquiring unit, both in the carbon dioxide gas concentration at carbon dioxide gas concentrations of 400 ppm and 1000 ppm.

Using the concentration calculation formula obtained in this way, gas concentration calculation at temperatures of 10° C., 25° C., and 40° C. in a dry environment (corresponding to a moisture absorption rate of 0% of the sealing portion) and gas concentration calculation at a temperature of 25° C. in a high humidity environment (corresponding to a moisture absorption rate of 100% of the sealing portion) were performed at carbon dioxide gas concentrations of 400 ppm, 1000 ppm, and 2000 ppm.

Figure 5:
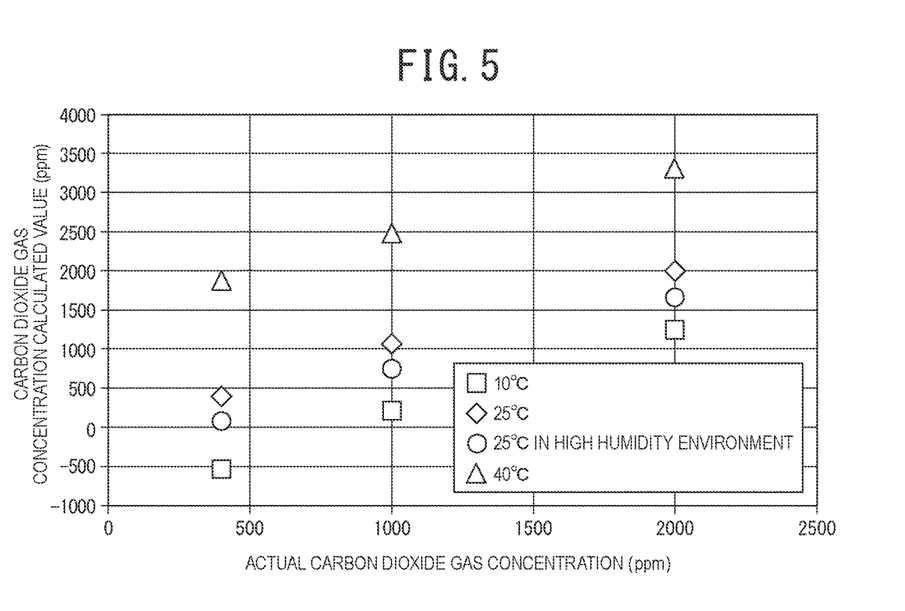
FIG. 5 is a diagram illustrative of a relationship between actual concentration of carbon dioxide gas and calculated values of carbon dioxide gas concentration in a comparative example.

FIG. 5 is a diagram illustrative of a relationship between actual concentration of carbon dioxide gas and calculated values of carbon dioxide gas concentration in the comparative example. In FIG. 5, the abscissa and the ordinate represent the actual concentration of carbon dioxide gas and the calculated values of carbon dioxide gas concentration, respectively. Square marks, rhombus marks, circle marks, and triangle marks illustrated in FIG. 5 indicate characteristics at 10° C. in the dry environment, characteristics at 25° C. in the dry environment, characteristics at 25° C. in the high humidity environment, and characteristics at 40° C. in the dry environment, respectively.

As illustrated in FIG. 4, when the gas concentration calculation formula obtained in the example is used, calculated values of carbon dioxide gas concentration, with respect to actual carbon dioxide gas concentrations, settled to errors of 64 ppm, 0 ppm, and 143 ppm at carbon dioxide gas concentrations of 400 ppm, 1000 ppm, and 2000 ppm, respectively.

On the other hand, as illustrated in FIG. 5, when the gas concentration calculation formula obtained in the comparative example is used, calculated values of carbon dioxide gas concentration, with respect to actual carbon dioxide gas concentrations, generated errors of 1469 ppm, 1473 ppm, and 1312 ppm at carbon dioxide gas concentrations of 400 ppm, 1000 ppm, and 2000 ppm, respectively.

From the results described above, it may be understood that a light receiving device, a light emitting device, and a light emitting and receiving device according to the present embodiment enable compensation for influence of temperature and humidity and, when, as an example, being applied to a gas concentration measuring apparatus, enable concentration calculation with higher accuracy than conventional gas concentration measuring apparatuses.

As described thus far, the present embodiment enables a light receiving device, a light emitting device, and a light emitting and receiving device in which influence of at least either temperature or humidity is compensated for and that have high accuracy to be achieved.

A light receiving device according to the present embodiment, when, for example, a light receiving element sealed using molded resin, which is an inexpensive package technology, is used, enables influence of temperature and humidity to be compensated for, which enables achievement of high accuracy. In addition, a light emitting device according to the present embodiment, when, for example, a light emitting element sealed using molded resin, which is an inexpensive package technology, is used, enables influence of temperature and humidity to be compensated for, which enables achievement of high accuracy. Further, a light emitting and receiving device according to the present embodiment, when, for example, a light receiving element and a light emitting element sealed using molded resin, which is an inexpensive package technology, are used, enables influence of temperature and humidity to be compensated for, which enables achievement of high accuracy.

Several aspects of the light emitting and receiving device will be hereinafter described.

(Aspect 1) A light emitting and receiving device including: a light emitting element; a light receiving element configured to receive at least a portion of light output by the light emitting element and output an output signal corresponding to amount of received light; a molded resin portion configured to seal at least a portion of the light emitting element; a temperature information acquiring unit configured to acquire temperature information; a humidity information calculating unit configured to calculate humidity information, based on information relating to at least either electrical characteristics or optical characteristics of the light emitting element and the temperature information; and a compensating unit configured to compensate the output signal, based on the temperature information and the humidity information.

(Aspect 2) A light emitting and receiving device including: a light emitting element; a light receiving element configured to receive at least a portion of light output by the light emitting element and output an output signal corresponding to amount of received light; a molded resin portion configured to seal at least a portion of the light receiving element; a temperature information acquiring unit configured to acquire temperature information; a humidity information calculating unit configured to calculate humidity information, based on information relating to at least either electrical characteristics or optical characteristics of the light receiving element and the temperature information; and a compensating unit configured to compensate the output signal, based on the temperature information and the humidity information.

(Aspect 3) A light emitting and receiving device including: a light emitting element; a light receiving element configured to receive at least a portion of light output by the light emitting element and output an output signal corresponding to amount of received light; a molded resin portion configured to seal at least a portion of the light emitting element; a temperature information acquiring unit configured to acquire temperature information; a humidity information calculating unit configured to calculate humidity information, based on information relating to at least either electrical characteristics or optical characteristics of the light emitting element and the temperature information; and a controlling unit configured to control the light emitting element, based on the temperature information and the humidity information.

(Aspect 4) A light emitting and receiving device including: a light emitting element; a light receiving element configured to receive at least a portion of light output by the light emitting element and output an output signal corresponding to amount of received light; a molded resin portion configured to seal at least a portion of the light receiving element; a temperature information acquiring unit configured to acquire temperature information; a humidity information calculating unit configured to calculate humidity information, based on information relating to at least either electrical characteristics or optical characteristics of the light receiving element and the temperature information; and a controlling unit configured to control the light emitting element, based on the temperature information and the humidity information.

(Aspect 5) The light emitting and receiving device according to any one of the above-mentioned aspects 1 to 4, wherein the temperature information includes information relating to at least one of temperature of the light receiving element, temperature of the light emitting element, and temperature of the molded resin portion, and the humidity information includes information relating to humidity of the molded resin portion.

(Aspect 6) The light emitting and receiving device according to any one of the above-mentioned aspects 1 to 5, wherein the temperature information includes at least either electrical characteristics or optical characteristics of at least either the light receiving element or the light emitting element.

(Aspect 7) The light emitting and receiving device according to any one of the above-mentioned aspects 1 to 6, wherein the molded resin portion includes: a light receiving side sealing region configured to seal at least a portion of the light receiving element; and a light emitting side sealing region configured to seal at least a portion of the light emitting element.

(Aspect 8) The light emitting and receiving device according to the above-mentioned aspect 7, wherein the light receiving side sealing region and the light emitting side sealing region are spatially in contact with each other.

(Aspect 9) The light emitting and receiving device according to the above-mentioned aspect 7 or 8, further comprising a light receiving side auxiliary element at least a portion of which is sealed by the light receiving side sealing region, wherein at least either the temperature information or the humidity information includes information relating to at least either electrical characteristics or optical characteristics of the light receiving side auxiliary element.

(Aspect 10) The light emitting and receiving device according to the above-mentioned aspect 9, wherein
the light receiving side auxiliary element is formed on a same light receiving side substrate as the light receiving element.

(Aspect 11) The light emitting and receiving device according to the above-mentioned aspect 9 or 10, wherein the light receiving side auxiliary element includes a diode structure or is a resistor, the diode structure including indium and at least either arsenic or antimony and including at least a P-type semiconductor layer and an N-type semiconductor layer.

(Aspect 12) The light emitting and receiving device according to any one of the above-mentioned aspects 7 to 11, further comprising a light emitting side auxiliary element at least a portion of which is sealed by the light emitting side sealing region, wherein at least either the temperature information or the humidity information includes information relating to at least either electrical characteristics or optical characteristics of the light emitting side auxiliary element.

(Aspect 13) The light emitting and receiving device according to the above-mentioned aspect 12, wherein the light emitting side auxiliary element is arranged on a same light emitting side substrate as the light emitting element.

(Aspect 14) The light emitting and receiving device according to the above-mentioned aspect 12 or 13, wherein the light emitting side auxiliary element includes a diode structure or is a resistor, the diode structure including indium and at least either arsenic or antimony and including at least a P-type semiconductor layer and an N-type semiconductor layer.

(Aspect 15) The light emitting and receiving device according to any one of the above-mentioned aspects 1 to 14, wherein the light receiving element includes a diode structure or is a resistor, the diode structure including indium and at least either arsenic or antimony and including at least a P-type semiconductor layer and an N-type semiconductor layer.

(Aspect 16) The light emitting and receiving device according to any one of the above-mentioned aspects 1 to 15, wherein the light emitting element includes a diode structure that includes indium and at least either arsenic or antimony and includes at least a P-type semiconductor layer and an N-type semiconductor layer.

The present invention was described above through embodiments thereof, but the technical scope of the present invention is not limited to that described in the above-described embodiments. The above-described embodiments may be subjected to various alterations and improvements, and it is apparent from the description in CLAIMS that embodiments subjected to such alterations and improvements may also be included in the technical scope of the present invention.

REFERENCE SIGNS LIST

1 Light receiving device
4 Light emitting device
5 Light emitting and receiving device
21, 51 Light receiving element
22, 42, 52 Molded resin portion
23, 43, 53 Temperature information acquiring unit
24, 44, 54 Humidity information calculating unit
25, 55 Compensating unit
26, 46 Substrate
27, 47 Auxiliary element
48, 58 Light emitting element
49, 59 Controlling unit
521 Light receiving side sealing region
522 Light emitting side sealing region
561 Light receiving side substrate
562 Light emitting side substrate
571 Light receiving side auxiliary element
572 Light emitting side auxiliary element

The invention claimed is:

1. A light receiving device comprising:
a light receiving element configured to receive at least a portion of light incident from an outside and output an output signal corresponding to amount of received light;
a molded resin portion configured to seal at least a portion of the light receiving element;
a temperature information acquiring unit configured to acquire temperature information relating to temperature of the light receiving element or temperature of the molded resin portion;
a measuring unit configured to measure information relating to at least one of electrical characteristics or optical characteristics of the light receiving element;
a humidity information calculating unit configured to calculate humidity information including information of the humidity of the molded resin portion, based on the information relating to the at least one of the electrical characteristics or the optical characteristics and the temperature information; and
a compensating unit configured to compensate the output signal, based on the temperature information and the humidity information.

2. The light receiving device according to claim 1, further comprising:
an auxiliary element, at least a portion of which being sealed by the molded resin portion,
wherein at least either the temperature information or the humidity information includes information relating to at least either electrical characteristics or optical characteristics of the auxiliary element.

3. The light receiving device according to claim 2, wherein:
the auxiliary element is on a same substrate as the light receiving element; and
the molded resin portion seals at least a portion of the substrate.

4. The light receiving device according to claim 2, wherein at least either the light receiving element or the auxiliary element includes a diode structure or is a resistor, the diode structure including indium and at least either arsenic or antimony, and including at least a P-type semiconductor layer and an N-type semiconductor layer.

5. The light receiving device according to claim 1, further comprising a temperature sensor configured to output the temperature information to the temperature information acquiring unit.

6. A light emitting and receiving device, comprising:
a light emitting element;
a light receiving element configured to receive at least a portion of light output by the light emitting element and output an output signal corresponding to amount of received light;
a molded resin portion configured to seal at least a portion of the light receiving element;
a temperature information acquiring unit configured to acquire temperature information including information relating to at least one of temperature of the light receiving element, temperature of the light emitting element, or temperature of the molded resin portion;
a measuring unit configured to measure information relating to at least one of electrical characteristics or optical characteristics of the light receiving element;
a humidity information calculating unit configured to calculate humidity information including information of the humidity of the molded resin portion, based on the information relating to the at least one of the electrical characteristics or the optical characteristics and the temperature information; and
a controlling unit configured to control the light emitting element, based on the temperature information and the humidity information.

7. The light emitting and receiving device according to claim 6, further comprising a temperature sensor configured to output the temperature information to the temperature information acquiring unit.

8. The light emitting and receiving device according to claim 6, wherein the temperature information includes at least either electrical characteristics or optical characteristics of at least either the light receiving element or the light emitting element.

9. The light emitting and receiving device according to claim 6, wherein the molded resin portion includes:
a light receiving side sealing region configured to seal at least a portion of the light receiving element; and
a light emitting side sealing region configured to seal at least a portion of the light emitting element.

10. The light emitting and receiving device according to claim 9, wherein the light receiving side sealing region and the light emitting side sealing region are spatially in contact with each other.

11. The light emitting and receiving device according to claim 9, further comprising:
a light receiving side auxiliary element at least a portion of which being sealed by the light receiving side sealing region, wherein at least either the temperature information or the humidity information includes information relating to at least either electrical characteristics or optical characteristics of the light receiving side auxiliary element.

12. The light emitting and receiving device according to claim 11, wherein the light receiving side auxiliary element is on a same light receiving side substrate as the light receiving element.

13. The light emitting and receiving device according to claim 11, wherein the light receiving side auxiliary element includes a diode structure or is a resistor, the diode structure including indium and at least either arsenic or antimony, and including at least a P-type semiconductor layer and an N-type semiconductor layer.

14. The light emitting and receiving device according to claim 9, further comprising:
a light emitting side auxiliary element at least a portion of which being sealed by the light emitting side sealing region,
wherein at least either the temperature information or the humidity information includes information relating to at least either electrical characteristics or optical characteristics of the light emitting side auxiliary element.

15. The light emitting and receiving device according to claim 14, wherein the light emitting side auxiliary element is on a same light emitting side substrate as the light emitting element.

16. The light emitting and receiving device according to claim 14, wherein the light emitting side auxiliary element includes a diode structure or is a resistor, the diode structure including indium and at least either arsenic or antimony, and including at least a P-type semiconductor layer and an N-type semiconductor layer.

17. The light emitting and receiving device according to claim 6, wherein the light receiving element includes a diode structure or is a resistor, the diode structure including indium and at least either arsenic or antimony, and including at least a P-type semiconductor layer and an N-type semiconductor layer.

18. The light emitting and receiving device according to claim 6, wherein the light emitting element includes a diode structure that includes indium and at least either arsenic or antimony, and includes at least a P-type semiconductor layer and an N-type semiconductor layer.

* * * * *

UNITED STATES PATENT AND TRADEMARK OFFICE
CERTIFICATE OF CORRECTION

PATENT NO. : 10,212,776 B2
APPLICATION NO. : 15/850271
DATED : February 19, 2019
INVENTOR(S) : Hiromi Fujita et al.

Page 1 of 1

It is certified that error appears in the above-identified patent and that said Letters Patent is hereby corrected as shown below:

In the Specification

Column 13, Lines 40-42, should read:
[Formula 1]
$$h(T) = A_1 \times T^2 + B_1 \times T + C_1$$

Signed and Sealed this
Eleventh Day of June, 2019

Andrei Iancu
*Director of the United States Patent and Trademark Office*